(12) United States Patent
Peikert et al.

(10) Patent No.: US 11,026,641 B2
(45) Date of Patent: Jun. 8, 2021

(54) SYSTEM AND METHOD FOR TOMOGRAPHY-BASED RADIOMIC MASS ANALYSIS

(71) Applicants: Mayo Foundation for Medical Education and Research, Rochester, MN (US); Vanderbilt University, Nashville, TN (US)

(72) Inventors: Tobias Peikert, Rochester, MN (US); Ronald A. Karwoski, Rochester, MN (US); Fabien Maldonado, Brentwood, TN (US); Srinivasan Rajagopalan, Chennai (IN); Brian J. Bartholmai, Rochester, MN (US)

(73) Assignees: Mayo Foundation for Medical Education and Research, Rochester, MN (US); Vanderbilt University, Nashville, TN (US)

(*) Notice: Subject to any disclaimer, the term of this patent is extended or adjusted under 35 U.S.C. 154(b) by 129 days.

(21) Appl. No.: 16/162,103

(22) Filed: Oct. 16, 2018

(65) Prior Publication Data
US 2019/0125279 A1    May 2, 2019

Related U.S. Application Data

(60) Provisional application No. 62/573,047, filed on Oct. 16, 2017.

(51) Int. Cl.
*A61B 6/03*    (2006.01)
*A61B 6/00*    (2006.01)
(Continued)

(52) U.S. Cl.
CPC .............. *A61B 6/032* (2013.01); *A61B 6/463* (2013.01); *A61B 6/466* (2013.01); *A61B 6/5217* (2013.01);
(Continued)

(58) Field of Classification Search
None
See application file for complete search history.

(56) References Cited

U.S. PATENT DOCUMENTS 6,738,499 B1    5/2004    Doi
7,664,604 B1 *  2/2010    Heine .................... G16H 50/20
                                                       702/19
(Continued)

OTHER PUBLICATIONS

Siegel RL, et al., Cancer Statistics, 2017. CA Cancer J Clin. 2017;67(1):7-30.

(Continued)

*Primary Examiner* — Fayyaz Alam
(74) *Attorney, Agent, or Firm* — Quarles & Brady LLP (57) ABSTRACT

Systems and methods are provided for classifying a tissue mass as malignant or benign. The method includes identifying a region of interest in the tissue mass in computed tomography (CT) imaging data, segmenting the CT imaging data to delimit at least a portion of the tissue mass into image segments, extracting a set of radiomic parameters indicative of the tissue mass. The set of radiomic parameters may include tissue mass location, tissue mass shape, tissue mass surface characteristic, or tissue mass texture distribution indicative of the amount of image segments identified. The method also includes generating a report classifying the indeterminate lung nodule as being malignant or benign based on the set of radiomic parameters of the indeterminate lung nodule.

20 Claims, 6 Drawing Sheets
(2 of 6 Drawing Sheet(s) Filed in Color)

(51) Int. Cl.
G06T 7/00 (2017.01)
A61B 8/13 (2006.01)
G06T 7/11 (2017.01)
(52) U.S. Cl.
CPC .............. *A61B 6/5229* (2013.01); *A61B 8/13* (2013.01); *G06T 7/0012* (2013.01); *G06T 7/11* (2017.01); *G06T 2207/10081* (2013.01); *G06T 2207/30064* (2013.01)

(56) References Cited

U.S. PATENT DOCUMENTS

| | | | | |
|---|---|---|---|---|
| 9,008,396 | B2* | 4/2015 | Haacke | G06T 7/0016 |
| | | | | 382/131 |
| 9,940,709 | B2 | 4/2018 | Gillies | |
| 2011/0075913 | A1* | 3/2011 | Moriya | G16H 30/40 |
| | | | | 382/132 |
| 2015/0356730 | A1* | 12/2015 | Grove | G06T 7/64 |
| | | | | 382/124 |
| 2016/0203599 | A1* | 7/2016 | Gillies | A61B 6/463 |
| | | | | 382/132 |
| 2018/0109698 | A1* | 4/2018 | Ramsay | G06K 9/4652 |
| 2020/0226779 | A1* | 7/2020 | Matsuzaki | A61B 6/032 |

OTHER PUBLICATIONS

National Lung Screening Trial Research Team, Aberle DR, et al. Reduced lung-cancer mortality with low-dose computed tomographic screening. N Engl J Med. 2011;365(5):395-409.
Tanoue LT, et al., Lung cancer screening. Am J Respir Crit Care Med. 2015;191(1):19-33.
Gould MK, et al. Recent Trends in the Identification of Incidental Pulmonary Nodules. Am J Respir Crit Care Med. 2015;192(10):1208-14.
Kauczor HU, et al. ESR/ERS white paper on lung cancer screening. Eur Radiol. 2015;25(9):2519-31.
Foley F, et al. Computer-Aided Nodule Assessment and Risk Yield Risk Management of Adenocarcinoma: The Future of Imaging? Semin Thorac Cardiovasc Surg. 2016;28(1):120-6.
Maldonado F, et al. Noninvasive characterization of the histopathologic features of pulmonary nodules of the lung adenocarcinoma spectrum using computer-aided nodule assessment and risk yield (CANARY)—a pilot study. J Thorac Oncol. 2013;8(4):452-60.
Maldonado F, et al. Noninvasive Computed Tomography-based Risk Stratification of Lung Adenocarcinomas in the National Lung Screening Trial. Am J Respir Crit Care Med. 2015;192(6):737-44.
Maldonado F, et al., Appreciating the shades of gray: a case for Computer-Aided Nodule Assessment and Risk Yield (CANARY)-based risk stratification of lung adenocarcinomas. J Thorac Dis. 2016;8(10):E1438-E40.
Raghunath S, et al. Noninvasive risk stratification of lung adenocarcinoma using quantitative computed tomography. J Thorac Oncol. 2014;9(11):1698-703.
Wilson R, et al., Radiomics of pulmonary nodules and lung cancer. Transl Lung Cancer Res. 2017;6(1):86-91.
Aerts HJ, et al. Decoding tumour phenotype by noninvasive imaging using a quantitative radiomics approach. Nat Commun. 2014;5:4006.
Grove O, et al. Quantitative computed tomographic descriptors associate tumor shape complexity and intratumor heterogeneity with prognosis in lung adenocarcinoma. PLoS One. 2015;10(3):e0118261.
Hawkins S, et al. Predicting Malignant Nodules from Screening CT Scans. J Thorac Oncol. 2016;11(12):2120-8.
Kalpathy-Cramer J, et al. Radiomics of Lung Nodules: A Multi-Institutional Study of Robustness and Agreement of Quantitative Imaging Features. Tomography. 2016;2(4):430-7.
Parmar C, et al. Radiomic feature clusters and prognostic signatures specific for Lung and Head & Neck cancer. Sci Rep. 2015;5:11044.
Wu W, et al. Exploratory Study to Identify Radiomics Classifiers for Lung Cancer Histology. Front Oncol. 2016;6:71.
National Lung Screening Trial Research Team, Aberle DR, et al. The National Lung Screening Trial: overview and study design. Radiology. 2011;258(1):243-53.
Pinsky PF, et al. Performance of Lung-Rads in the National Lung Screening Trial: a retrospective assessment. Ann Intern Med. 2015;162(7):485-91.
MacMahon H, et al. Guidelines for Management of Incidental Pulmonary Nodules Detected on CT Images: From the Fleischner Society 2017. Radiology. 2017:161659.
Daly S, et al. Development and validation of a plasma biomarker panel for discerning clinical significance of indeterminate pulmonary nodules. J Thorac Oncol. 2013;8(1):31-6.
Ferguson JS, et al. Impact of a bronchial genomic classifier on clinical decision making in patients undergoing diagnostic evaluation for lung cancer. BMC Pulm Med. 2016;16(1):66.
Silvestri GA, et al. A Bronchial Genomic Classifier for the Diagnostic Evaluation of Lung Cancer. N Engl J Med. 2015;373(3):243-51.
Sozzi G, et al. Clinical utility of a plasma-based miRNA signature classifier within computed tomography lung cancer screening: a correlative MILD trial study. J Clin Oncol. 2014;32(8):768-73.
Vachani A, et al. Validation of a multiprotein plasma classifier to identify benign lung nodules. J Thorac Oncol. 2015;10(4):629-37.
Vachani A, et al. Clinical Utility of a Bronchial Genomic Classifier in Patients With Suspected Lung Cancer. Chest. 2016;150(1):210-8.
Maldonado, F., et al., Noninvasive Characterization of Indeterminate Pulmonary Nodules Detected on Chest High-Resolution Computed Tomography, US Army Medical Research and Materiel Command, Jan. 2017.
Peikert T, et al. (2018) Novel high-resolution computed tomography-based radiomic classifier for screen-identified pulmonary nodules in the National Lung Screening Trial. PLoS ONE 13(5): e0196910.

* cited by examiner

SYSTEM AND METHOD FOR TOMOGRAPHY-BASED RADIOMIC MASS ANALYSIS

CROSS-REFERENCE TO RELATED APPLICATIONS

This application claims the benefit of U.S. Provisional Patent Application Ser. No. 62/573,047, filed on Oct. 16, 2017, which is herein incorporated by reference in its entirety.

STATEMENT REGARDING FEDERALLY SPONSORED RESEARCH

This invention was made with government support under W81XWH-15-1-0110 awarded by the U.S. Army. The government has certain rights in the invention.

BACKGROUND

With approximately 160,000 deaths every year in the US, lung cancer continues to account for more annual cancer-related deaths than colon, prostate, and breast cancer combined. In 2011, the National Lung Screening Trial (NLST) demonstrated a 20% relative reduction in lung cancer mortality with annual low-dose computed tomography (LDCT). These encouraging results triggered the widespread endorsement of lung cancer screening. However, large-scale implementation has been hampered by the high rate of false-positive LDCT studies. In the NLST approximately 40% of individuals randomized to high-resolution computed tomography (HRCT) screening had one or more pulmonary nodules identified during the study period, 96% of which were ultimately proven benign.

In addition, the increasing utilization of diagnostic chest computed tomography (CT) already results in an estimated 1.5 million incidentally discovered indeterminate lung nodules in the US annually. With the implementation of LDCT lung cancer screening for the >10 million US adults meeting the screening eligibility criteria, this number is estimated to increase substantially.

The increased detection of indeterminate pulmonary nodules in the absence of reliable non-invasive strategies to differentiate benign and malignant nodules will almost certainly result in an increase in iatrogenic mortality, treatment related morbidity, and health care costs. While unnecessary invasive diagnostic and therapeutic interventions were kept to a minimum in the NLST study, the management of indeterminate pulmonary nodules in clinical practice serving the general population remains a major challenge.

Clinical risk calculators have significantly improved the management of indeterminate pulmonary nodules, but additional tools to distinguish benign from malignant nodules are needed, especially for intermediate risk pulmonary nodules, in order to minimize patient anxiety, radiation exposure, health care costs, and procedural morbidity and mortality. Furthermore, lung cancer is but a single example of the various forms of cancer, many of which suffer from similar challenges with distinguishing benign masses from malignant masses.

SUMMARY

The present disclosure overcomes the aforementioned drawbacks by providing a variety of systems and methods. In accordance with one aspect of the disclosure, a method is provided for generating an imaging report indicating an indeterminate nodule in a subject's lung as malignant or benign by performing a quantitative analysis on a computed tomography (CT) image of the subject. The method includes (a) identifying, using a computer system, a region of interest in the CT image that includes the indeterminate lung nodule, (b) segmenting, using the computer system, the image to delimit at least a portion of the region of interest into segments, and (c) tagging, using the computer system, at least a portion of the image segments based on an initial radiomic parameter value. The method also includes (d) identifying, using the computer system, image segments in the region of interest that have a radiomic parameter value similar to the initial radiomic parameter value of the tagged image segments of step (c) using a similarity metric. The method further includes (e) determining, using the computer system, an amount of identified image segments in the region of interest that have the radiomic parameter value that is similar to the initial radiomic parameter value. The method also includes (f) extracting, using the computer system, a set of radiomic parameters indicative of the indeterminate lung nodule. The set of radiomic parameters can include one or more nodule location parameter, one or more nodule shape parameter, one or more nodule surface characteristic parameter, and one or more nodule texture distribution parameter indicative of the amount of image segments identified in step (e). The method then includes (g) generating, using the computer system, a report classifying the indeterminate lung nodule as being malignant or benign based on the set of radiomic parameters.

In accordance with another aspect of the disclosure, a method is provided for classifying an indeterminate lung nodule in a subject as malignant or benign by performing a quantitative analysis on computed tomography (CT) imaging data of the subject's lung. The method includes using a processor to perform steps including identifying a region of interest in the indeterminate lung nodule in the CT imaging data and segmenting the CT imaging data to delimit at least a portion of the indeterminate lung nodule into image segments. The method also includes extracting a set of radiomic parameters indicative of the indeterminate lung nodule, wherein the set of radiomic parameters include one or more nodule location parameter that includes an offset coordinate location associated with a centroid of the indeterminate lung nodule within the CT imaging data, wherein the offset coordinate location is identified relative to an origin in the CT imaging data. The set of radiomic parameters can also include one or more nodule texture parameter, two nodule shape parameters, and four nodule surface characteristic parameters. The method includes generating a report classifying the indeterminate lung nodule as being malignant or benign based on the set of radiomic parameters of the indeterminate lung nodule.

In accordance with yet another aspect of the disclosure, a system is provided that includes a memory having stored therein computed tomography images of a subject and a processor configured to access the memory. The processor is configured to carry out steps that include (a) identify a region of interest in the CT images that includes a tissue mass, (b) segment the images to delimit at least a portion of the region of interest into segments, and (c) tag at least a portion of the image segments based on an initial radiomic parameter value. The process or is also configured to (d) identify image segments in the region of interest that have a radiomic parameter value similar to the initial radiomic parameter value of the tagged image segments of step (c) using a similarity metric and (e) determine an amount of identified image segments in the region of interest that have the radiomic parameter value that is similar to the initial radiomic parameter value. The processor is further configured to (f) extract a set of radiomic parameters indicative of the tissue mass. The set of radiomic parameters can include one or more of tissue mass location, tissue mass shape, tissue mass surface characteristic, or tissue mass texture distribution indicative of the amount of image segments identified in step (e). The processor is also configured to (g) generate a report classifying the indeterminate lung nodule as being malignant or benign based on the set of radiomic parameters.

The foregoing and aspects of the disclosure of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
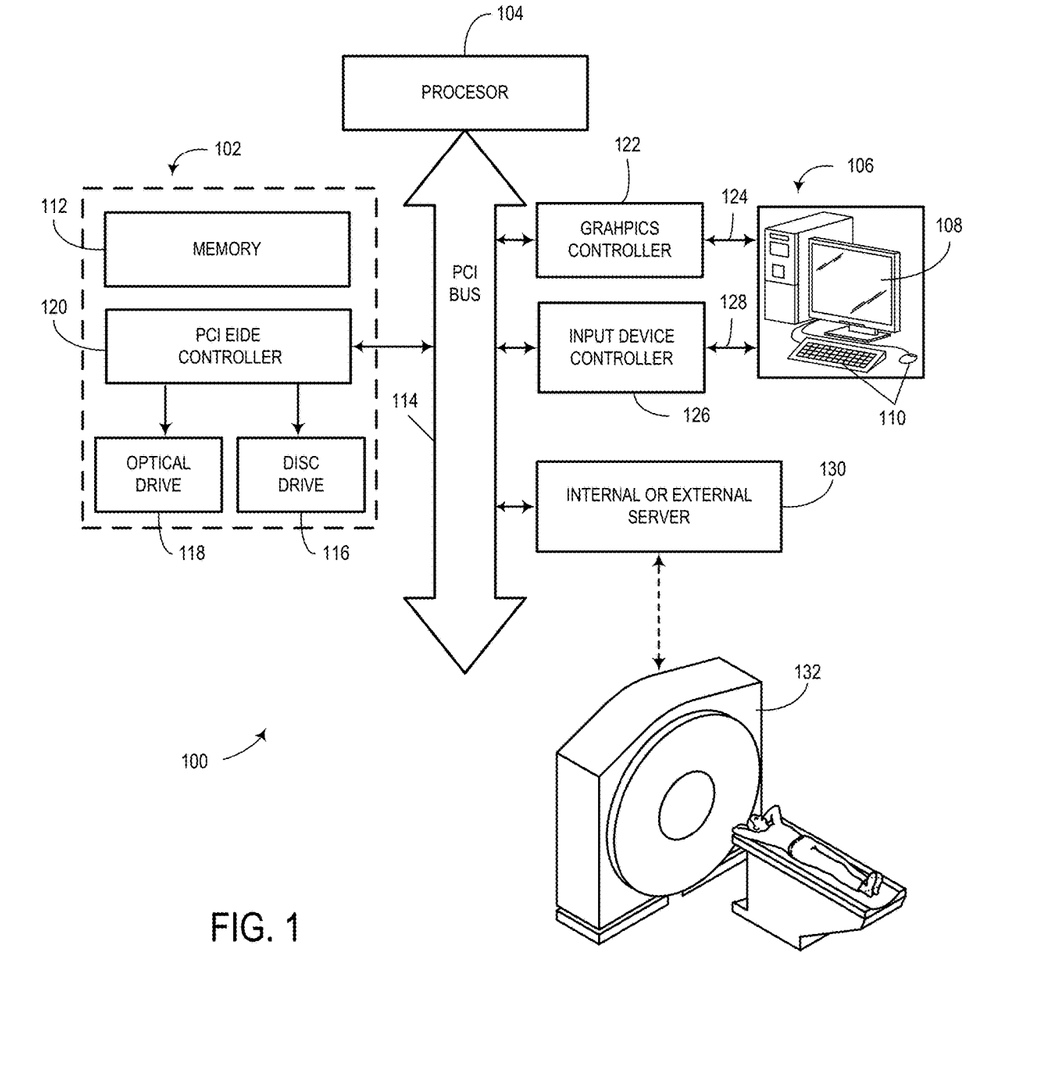
FIG. 1 is a block diagram of a computer system in accordance with the present disclosure.

Referring now to FIG. 1, a computer system 100 that can perform the methods described in the present disclosure is illustrated. In general, the computer system 100 includes a memory workstation 102, a processor 104, and an operator workstation 106 that may include a display 108 and one or more input devices 110 (e.g., a keyboard, a mouse, a touch screen).

The processor 104 is a commercially available programmable machine running on a commercially available operating system. For example, the processor 104 may include internal memory and I/O control to facilitate system integration and integral memory management circuitry for handling all external memory 112. The processor 104 also has access to a peripheral component interconnect (PCI) bus driver that facilitates interfacing with a PCI bus 114. The processor 104 may operate autonomously or semi-autonomously. The processor 104 may read executable software instructions from the memory 112, or a computer-readable medium (e.g., disc drive 116, optical drive 118, hard drive, flash memory). The processor 104 may also receive instructions via the one or more input devices 110 from the user, or another source logically connected to a computer or device, such as another networked computer or server.

The PCI bus 114 is an industry standard bus that transfers data between the processor 104 and a number of peripheral controller cards. These may include a PCI enhanced integrated drive electronics (EIDE) controller 120 which provides a high-speed transfer of data to and from an optical drive 118 (e.g., CD-ROM drive) and a disc drive 116. A graphics controller 122 may be used to couple the PCI bus 114 to the display 108 through a standard display connection 124, and an input device controller 126 receives data from the one or more input devices 110, such as a mouse or a keyboard, through respective connection 128.

In some embodiments, the display 108 may be a monitor, which presents an image measurement graphical user interface (GUI) that allows a user to input parameters into the workstation 106. The input parameters may take any suitable shape or form, as desired, for operation of the computer system 100, including the ability for selecting, entering or otherwise specifying parameters consistent with processing tasks, processing data, or operating the computer system 100. The computer system 100 may receive data, such as medical imaging data, from an internal or external server 130, for example, from a department picture archiving and communication system (PACS), an institution image management system, or other source capable of transferring medical imaging data. In some embodiments, the computer system 100 is directly connected to a medical imaging system 132, such as an x-ray computed tomography ("CT") imaging system, such as the system described in FIGS. 2A and 2B.

In some embodiments, the computer system 100 can be implemented, for example, by a workstation, a notebook computer, a tablet device, a mobile device, a multimedia device, a network server, a mainframe, one or more controllers, one or more microcontrollers, or any other general-purpose or application-specific computing device.

Figure 2A:
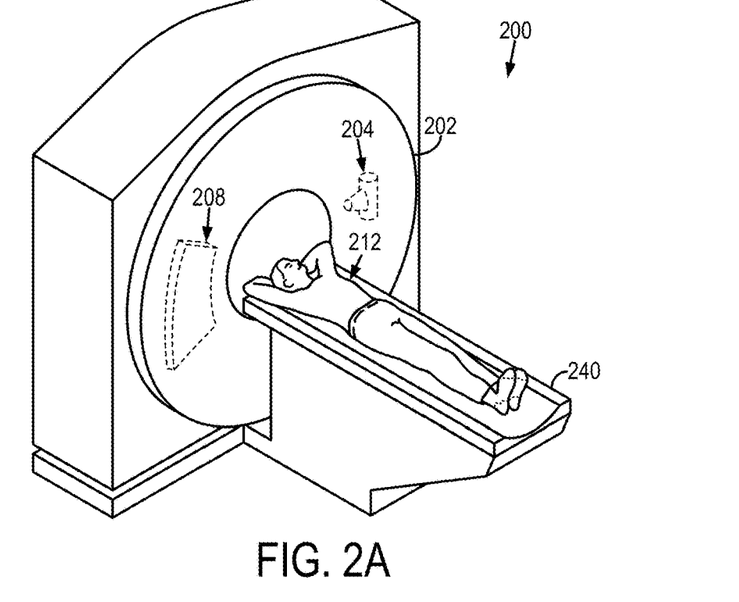
FIG. 2A is an illustration of an x-ray computed tomography (CT) imaging system in accordance with the present disclosure.
Figure 2B:
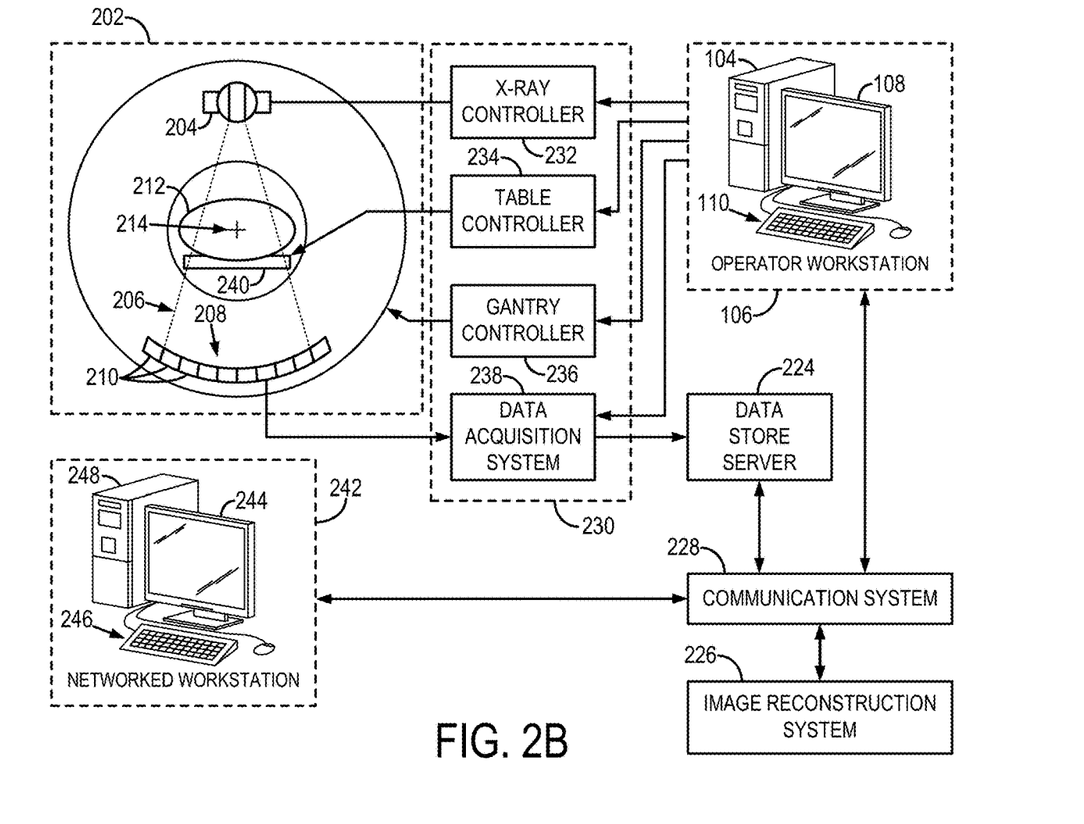
FIG. 2B is a block diagram of the CT imaging system in accordance with the present disclosure.

Referring particularly now to FIGS. 2A and 2B, an example of an x-ray CT imaging system 200 that may be used to implement the methods in accordance with the present disclosure. The CT system includes a gantry 202, to which at least one x-ray source 204 is coupled. The x-ray source 204 projects an x-ray beam 206, which may be a fan-beam or cone-beam of x-rays, towards a detector array 208 on the opposite side of the gantry 202. The detector array 208 includes a number of x-ray detector elements 210. Together, the x-ray detector elements 210 sense the projected x-rays 206 that pass through a subject 212, such as a medical patient or an object undergoing examination that is positioned in the CT system 200. Each x-ray detector element 210 produces an electrical signal that may represent the intensity of an impinging x-ray beam and, hence, the attenuation of the beam as it passes through the subject 212. In some configurations, each x-ray detector 210 is capable of counting the number of x-ray photons that impinge upon the detector 210. During a scan to acquire x-ray projection data, the gantry 202 and the components mounted thereon rotate about a center of rotation 214 located within the CT system 200.

The CT system 200 also includes an operator workstation 106, which typically includes the display 108; one or more input devices 110, such as a keyboard and mouse; and a computer processor 104, as described in FIG. 1. The operator workstation 106 provides the operator interface that enables scanning control parameters to be entered into the CT system 200. In general, the operator workstation 106 is in communication with a data store server 224 and an image reconstruction system 226. By way of example, the operator workstation 216, data store server 224, and image reconstruction system 226 may be connected via a communication system 228, which may include any suitable network connection, whether wired, wireless, or a combination of both. As an example, the communication system 228 may include both proprietary or dedicated networks, as well as open networks, such as the internet.

The operator workstation 106 is also in communication with a control system 230 that controls operation of the CT system 200. The control system 230 generally includes an x-ray controller 232, a table controller 234, a gantry controller 236, and a data acquisition system 238. The x-ray controller 232 provides power and timing signals to the x-ray source 204 and the gantry controller 236 controls the rotational speed and position of the gantry 202. The table controller 234 controls a table 240 to position the subject 212 in the gantry 202 of the CT system 200.

The DAS 238 samples data from the detector elements 210 and converts the data to digital signals for subsequent processing. For instance, digitized x-ray data is communicated from the DAS 238 to the data store server 224. The image reconstruction system 226 then retrieves the x-ray data from the data store server 224 and reconstructs an image therefrom. The image reconstruction system 226 may include a commercially available computer processor, or may be a highly parallel computer architecture, such as a system that includes multiple-core processors and massively parallel, high-density computing devices. Optionally, image reconstruction can also be performed on the processor 104 in the operator workstation 106. Reconstructed images can then be communicated back to the data store server 224 for storage or to the operator workstation 106 to be displayed to the operator or clinician.

The CT system 200 may also include one or more networked workstations 242. By way of example, a networked workstation 242 may include a display 244; one or more input devices 246, such as a keyboard and mouse; and a processor 248. The networked workstation 242 may be located within the same facility as the operator workstation 216, or in a different facility, such as a different healthcare institution or clinic.

The networked workstation 242, whether within the same facility or in a different facility as the operator workstation 106, may gain remote access to the data store server 224 and/or the image reconstruction system 226 via the communication system 228. Accordingly, multiple networked workstations 242 may have access to the data store server 224 and/or image reconstruction system 226. In this manner, x-ray data, reconstructed images, or other data may be exchanged between the data store server 224, the image reconstruction system 226, and the networked workstations 242, such that the data or images may be remotely processed by a networked workstation 242. This data may be exchanged in any suitable format, such as in accordance with the transmission control protocol ("TCP"), the internet protocol ("IP"), or other known or suitable protocols.

Figure 3:
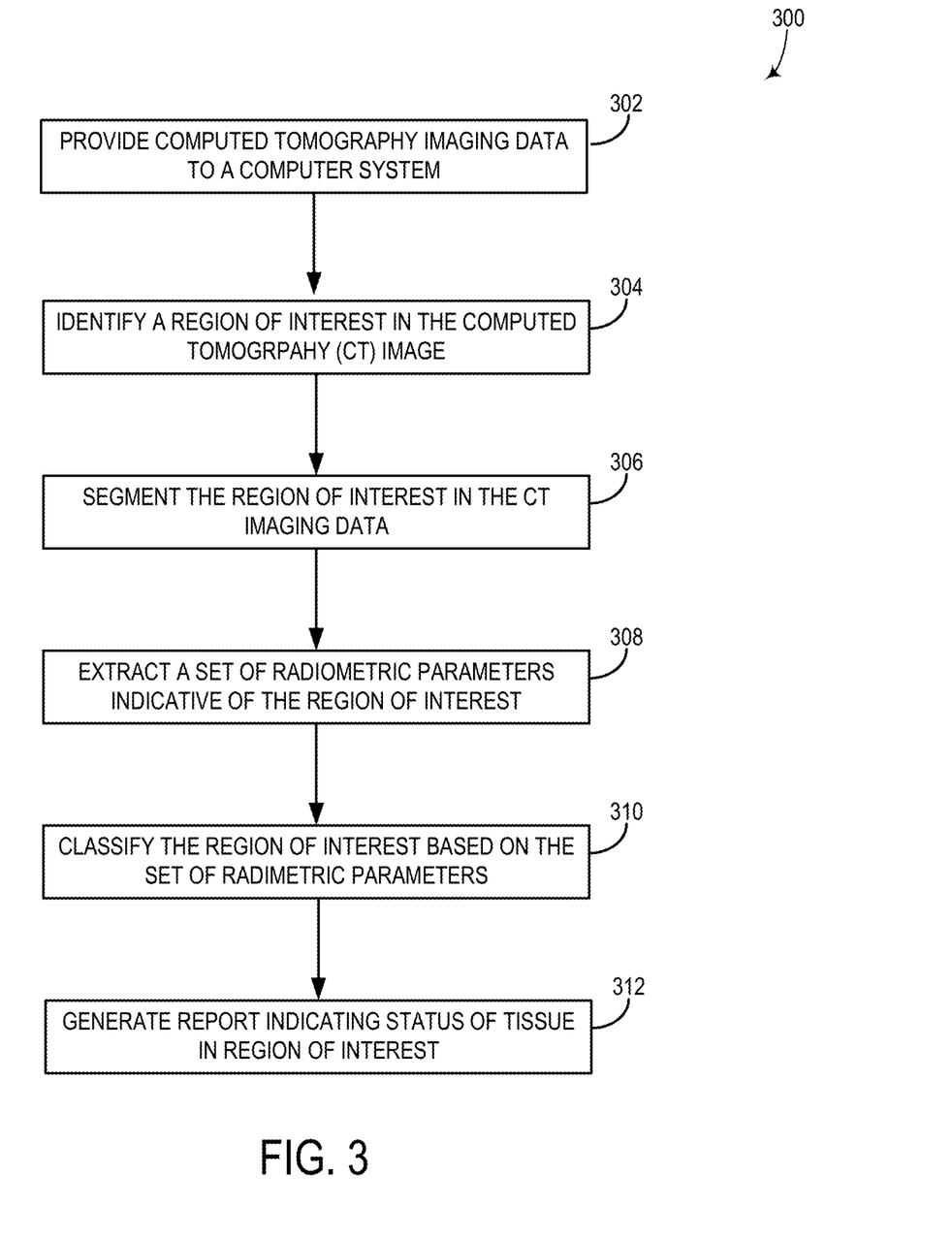
FIG. 3 is a flowchart setting forth some examples of steps of one method for classifying non-invasively assessing a mass in a subject as malignant or benign from CT imaging data in accordance with the present disclosure.

Referring now to FIG. 3, some examples steps of a method 300 that may employ or use data acquired by the computer system 100 or the CT imaging system 200 of FIGS. 1, 2A, and 2B are provided. As will be described, the method 300 can be used to classify a tissue mass, such as an indeterminate nodule in a subject's lung, as malignant or benign by performing a analysis on a computed tomography image. The method 300 will be described with respect to FIG. 3 and also FIG. 4A, FIG. 4B, and FIG. 4C.

Referring now to FIG. 3, the method 300 begins at process step 302 by providing CT imaging data to a computer system programmed as will be described. The CT imaging data can be provided to the computer system by retrieving previously acquired CT imaging data from the memory or other data storage device. The CT imaging data can also be provided to the computer system by acquiring the CT imaging data using the CT imaging system, such as described above, and communicating the acquired data to the computer system, which may form part of the CT imaging system. The computer system may process the CT imaging data to render a CT image or the data provided to the computer system may be data that was previously reconstructed.

As indicated at process block 304, the method 300 includes identifying a region of interest in the image. In some aspects, the region of interest may include an indeterminate lung nodule. In other aspects, the region of interest may includes an indeterminate lung nodule and surrounding tissue, among other tissue types (intruding vessels, pleura, etc.) or may not include the lung or lung nodules, but include tissue masses located in other areas of the body or associated with other organs, including the brain, liver, kidney, throat, chest, abdomen, or the like.

Figure 4A:
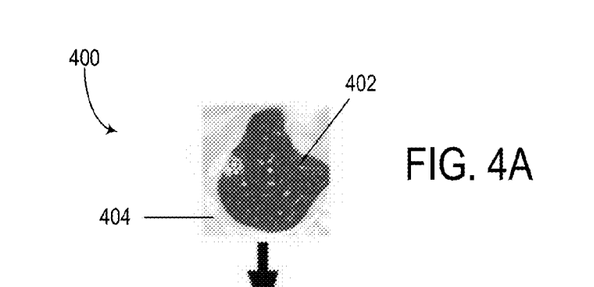
FIG. 4A is a CT image illustrating a region of interest within a subject's lung that includes a mass in the form of an indeterminate nodule acquired in accordance with the present disclosure.
Figure 4B:
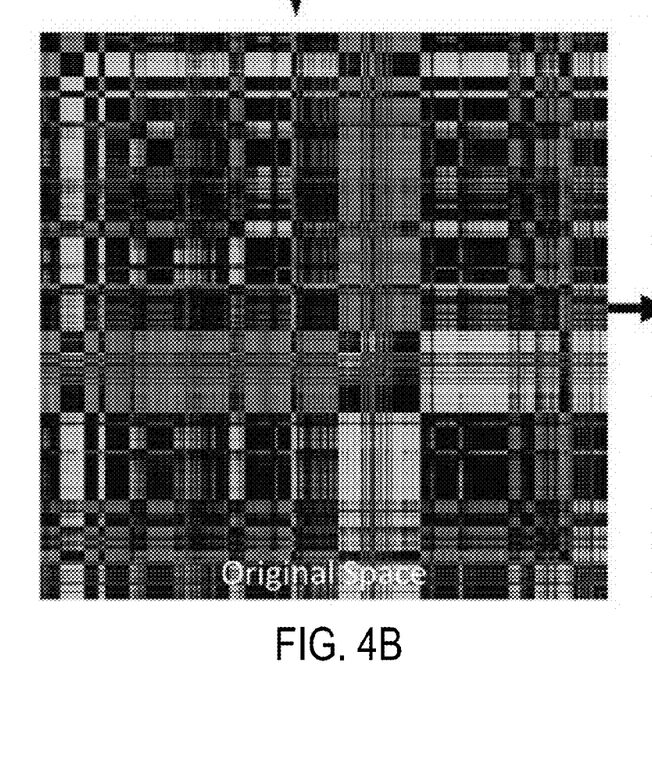
FIG. 4B is an enlarged view of a region of interest within the indeterminate nodule from the CT image in FIG. 4A.

As a non-limiting example, referring to FIG. 4A, a non-limiting example of a CT image 400 is shown having a region of interest that includes an indeterminate lung nodule 402 and surrounding tissue 404. As shown in FIG. 4B, which is an enlarged view of a section of FIG. 4A, indeterminate lung nodules and surrounding tissues may include at least one radiomic parameter that varies across the region of interest (e.g., image intensity values).

Referring back to FIG. 3, the method 300 further includes performing segmentation to delimit at least a portion of the region of interest into image segments 406, as indicated at process block 306. The segmentation may be performed automatically by a computer. Additionally or alternatively, a clinician may provide input on the segmentation. In the non-limiting example in FIG. 4C, image segments 406 may be of varying size, and may comprise a single voxel or a plurality of voxels within the region of interest. The indeterminate lung nodule may be segmented manually, semi-automatically, or automatically. Manual editing may be performed to remove, if needed, intruding structures, such as vessels and pleura.

Figure 4C:
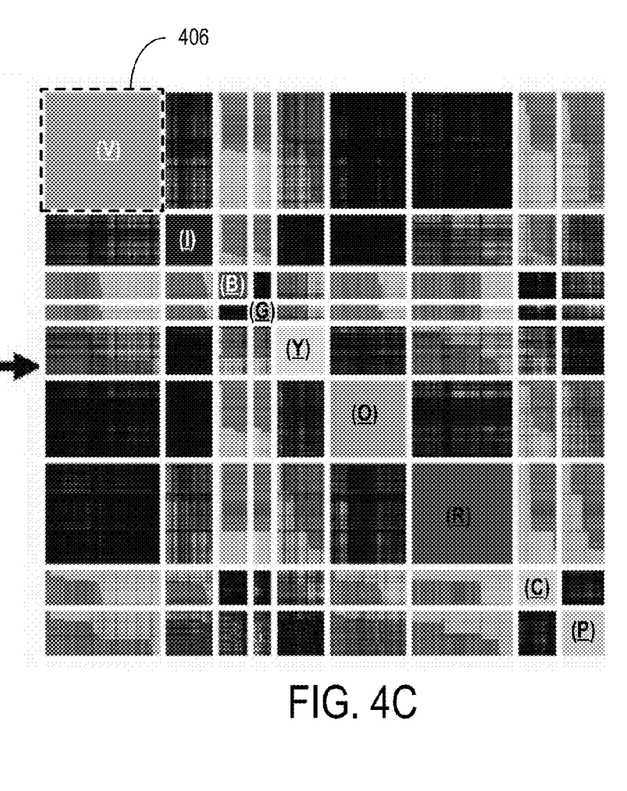
FIG. 4C is a non-limiting example of processing an image in accordance with the present disclosure.

Specifically, FIG. 4C illustrates a non-limiting example of tagging the image segments 406. For example, FIG. 4C shows nine image segments 406 that are color-coded as Violet (V), Indigo (I), Blue (B), Green (G), Yellow (Y), Orange (O), Red (R), Cyan (C) and Pink (P). These color-coded texture exemplars can be used to form basic building blocks for the analysis and risk stratification of the indeterminate nodules. Based on this, the nine texture exemplars arbitrarily labeled as V, I, B, G, Y, O, R, C, and P can be ordinated as V-R-O-I-Y-P-B-G-C. Such surface exemplars can be ordinated as unknown-minimal surface-valley-flat-ridge-pit-saddle valley-saddle ridge-peak. A metric, such as Score Indicative of Lesion/Lung Aggression/Abnormality" (SILA), as will be described below, can be computed. SILA can be computed as the Cramer-Von Mises Distance of the ordinated exemplar distributions. Using a similar strategy, the exemplars (such as Normal, Ground Glass, Honeycombing, Reticular, {mild, moderate, severe} lower attenuation areas for seven primal parenchymal) can be ordinated to compute the SILA for the areas surrounding the mass.

In one aspect, the indeterminate lung nodule or other masses may be segmented, for example, using a suitable software such as an ANALYZE software (Biomedical Imaging Resource, Mayo Clinic, Rochester, Minn.). During segmentation, the location and the dimensions of each nodule is identified and a stack of two dimensional borders are traced out along the transverse orientation. Tracing errors can be minimized by guiding the traces along automatically-detected edges. Apart from being very labor intensive and subjective, manual approaches may suffer from out-of-plane discontinuities arising due to section-by-section two dimensional delineation of a three dimensional object.

The indeterminate lung nodule or other masses may be automatically or semi-automatically segmented using a region growing approach. For example, a region growing system may receive an operator-specified bounding cube that encloses the indeterminate nodule or other mass and a seed location. In one aspect, a radiomic feature is recorded at the seed location, and the radiomic feature from the seed location is compared to other candidate image segments based on a pair-wise similarity score between the initial value of the radiomic feature and the candidate image segment. To identify the similarity metric that best characterizes a match, a multi-dimensional scaling (MDS) may be used to project pairwise similarities between each of the voxels or image segments 406.

Thus, a multivariate similarity measure can be projected into three dimensions (3D), to visualize trends and groupings. In this way, a 3D multivariate similarity measure can be achieved. Using the pairwise similarity matrix, MDS positions the data such that the Euclidean distances (other distances are also possible) between all pairs of the points in this plot reflect the observed distances as faithfully as possible. Parametric and non-parametric similarity metrics supported in "Volumetrics", developed as a plug-in module in the Analyze software from Mayo Clinic in Rochester, Minn., can be used. As a non-limiting example, parametric metrics can include first and second order statistics and measures of effectiveness, such as Fechner-Weber contrast measure, target-reference inference ratio, Fisher distance, and the like. Non-parametric similarity metrics can be based on histogram distances, such as Manhattan, Euclidean, Bhattacharya, Kolmogrov-Smirnoff, and Cramer Von Mises (CVM) distance. In many configurations, MDS representation of CVM (the squared L2-metric between cumulative density functions) can be advantageously consistent with expert groupings.

In one non-limiting example, the radiomic feature in the seed location may be based on a texture classification. The texture classification may be calculated using the computer aided lung informatics for Pathology Evaluation and Rating (CALIPER) software (Mayo Clinic, Rochester, Minn.). The detection and quantification of pulmonary parenchyma on CT scans by CALIPER is based on histogram signature mapping techniques trained through expert radiologist consensus assessment of pathologically confirmed training sets. For example, using CALIPER, the candidate texture features for parametric region growing can be identified based on the signatures of a multitude of manually segmented nodules derived from the Mayo training, discovery, and NLST lung cancer cohort. The identified candidate textual features are then provided to an input of a classifier that is subsequently trained to reproduce the expert labels. Thus, segmentation can be highly or completely automated.

As indicated by process block 310, the indeterminate lung nodule is then classified as being malignant or benign based on the set of radiomic parameters using the computer system 100. In one aspect, classifying the indeterminate nodule includes applying the set of radiomic parameters to a multivariate predictive model, which is further detailed in the examples below.

As indicated by process block 308, a set of radiomic parameters can be extracted from the region of interest in the segmented images. The set of radiomic parameters may include, as non-limiting examples, one or more parameters associated with a spatial location of the nodule, a size of the nodule, a shape of the nodule, a radiodensity (e.g., image intensity based on CT Hounsfield units), a nodule texture, a nodule texture distribution parameter indicative of the amount of identified image segments in the region of interest (e.g., nodule texture metric based on the texture exemplar distribution within the nodule), a nodule density, a density exemplar distribution within one or more clustered region within the nodule, a texture of the surrounding tissue around the nodule, a density of the surrounding tissue around the nodule, nodule surface descriptors, and nodule surface exemplar distribution within one or more clustered region within the nodule, mixtures, and combinations thereof. A non-exhaustive list of radiomic parameters suitable for use in method 300 are listed and described in Table 1. A few of the radiomic parameters, such as the one or more surface characteristic and the nodule texture parameters, are further detailed below.

TABLE 1

| Metric Category | # | Radiomic parameter | Non-Limiting Exemplary Description of radiomic parameter |
|---|---|---|---|
| Shape | 1 | Volume (V) | Nodule volume (e.g., mm$^3$) |
| | 2 | Surface Area (S) | Surface area (e.g., mm$^2$). Contribution of each surface voxel is determined by the neighbors of that voxel. Additionally, the surfaces which intersect the edge of the volume are included in the measurements. |
| | 3 | Sphericity (Sph) | $$Sph = \frac{6 * \sqrt{\pi V}}{S^{3/2}}$$ |

TABLE 1-continued

| Metric Category | # | Radiomic parameter | Non-Limiting Exemplary Description of radiomic parameter |
|---|---|---|---|
| | 4 | Sphere Fit Factor (SFF) | $SFF = \dfrac{S^3}{\pi(2V/3)^2}$ |
| | 5 | Radius (R) | Maximum radius if it were to be spherical $$\text{nodule } R = \left(\dfrac{3V}{4\pi}\right)^{1/3}$$ |
| | 6 | Minimum Enclosing Brick (MEB) | The x and/or y and/or z coordinates of the minimum enclosing brick around the nodule (e.g., a circumference for 2-dimensional data or a volume for 3-dimensional data) |
| | 7 | MEB | The orientation of the minimum enclosing brick around the nodule. |
| | 8 | Elongation (E) | $E = 1.0 - \dfrac{\varepsilon\_max}{\varepsilon\_mid}$ $\varepsilon\_max$, $\varepsilon\_mid$ are the maximum and middle edge lengths of MEB |
| | 9 | Flatness (F) | $F = 1.0 - \dfrac{\varepsilon\_mid}{\varepsilon\_min}$ $\varepsilon\_min$, $\varepsilon\_mid$ are the minimum and middle edge lengths of MEB |
| Intensity | 10 | Mean (Avg) | average of the voxel intensities within the nodule |
| | 11 | Variance (Var) | variance the voxel intensities within the nodule |
| | 12 | Skew (Skew) | skewness of the voxel intensities within the nodule $$Skew = \dfrac{\dfrac{\Sigma(x_i - Avg)^3}{N}}{Var^{3/2}}$$ |
| | 13 | Kurtosis (Kur) | Kurtosis of the voxel intensities within the nodule $$Kur = \dfrac{\dfrac{\Sigma(x_i - Avg)^4}{N}}{Var^2}$$ |
| | 14 | Entropy (En) | $En = -x_i * \log2(x_i)$ |
| Location | 15 | Location (Loc) | A weighted value or quantitative value assigned to indeterminate nodules positioned in the Left/Right (L/R), Upper/Middle/Lower (U/M/L), Peripheral/Central (P/C) region of the subject's lung. |
| | 16 | Offset from an origin in imaging data, such as a subject's Carina | x and/or y and/or z coordinate offsets of the nodule centroid relative to the origin, where the origin is taken as the Carina in the subject's lung. |
| | 17 | Offset from an origin in imaging data, such as a subject's Hila | x and/or y and/or z coordinate offsets of the nodule centroid relative to the origin, where the origin is taken as the Hila in the subject's lung. |
| | 18 | Offset from an origin in imaging data, such as a subject's Pleura | x and/or y and/or z coordinate offsets of the nodule centroid relative to the origin, where the origin is taken as the Pleura in the subject's lung. |
| Nodule Texture | 19 | Exemplar Distribution | Distribution of one or more CANARY texture exemplars constituting the nodule. |
| | 20 | SILA | Score Indicative of Lesion Aggression for the nodule texture. |
| | 21 | Risk Category | Risk Stratification group. |
| Nodule Surround Texture | 22 | Surround Distribution | Distribution of the parenchymal exemplars (Normal, Honey comb, Reticular, Ground glass, mild low attenuation area (LAA), moderate LAA, severe LAA) within a distance, such as 10 mm around the nodule. |
| | 23 | Percentage Vessels | Percentage of Vessels within a distance, such as 10 mm region, around the nodule |

TABLE 1-continued

| Metric Category | # | Radiomic parameter | Non-Limiting Exemplary Description of radiomic parameter |
|---|---|---|---|
| | 24 | Percentage Background | Percentage of non-lung voxels around the nodule |
| | 25 | SILA_Fib | SILA score for the distribution of honey comb, reticular and ground glass surrounding the nodule. |
| | 26 | SILA_LAA | SILA score for the distribution of mild, moderate and severe LAA. |
| Nodule Surface | 27 | Number of Vertices NV | Number of vertices in the surface |
| | 28 | Willmore Bending Energy (WEB) | Given the per-vertex principal curvatures $k_1$ and $k_2$, WEB = $\int_A (k_1^2 + k_2^2)\, dA$ |
| | 29 | Mean Curvature (H): Min | Mean curvature (H) is an extrinsic curvature that arises from the mechanical folding of the surface. |
| | 30 | H: (max) Maximum mean curvature | |
| | 31 | H: (−ve Avg) Average negative value curvature | $H = \dfrac{(k_1 + k_2)}{2};$ |
| | 32 | H: (+ve Avg) Average positive value curvature | where $k_1$ and $k_2$ are the per-vertex principal curvatures. |
| | 33 | H: (−ve Skew) Average negative value skew curvature | |
| | 34 | H: (+ve Skew) | |
| | 35 | Gaussian Curvature (G): Min | Gaussian Curvature (G) $G = k_1 * k_2;$ where $k_1$ and $k_2$ are the per-vertex principal curvatures. |
| | 36 | G: Max | |
| | 37 | G: −ve Avg | |
| | 38 | G: +ve Avg | |
| | 39 | G: −ve Skew | |
| | 40 | G: +ve Skew | |
| | 41 | Sharpness (S): Min | Sharpness at a vertex emphasizes regions where k1 and k2 are maximally different as in the crests and depths. $S_i = (k_1^2 - k_2^2);$ where $k_1$ and $k_2$ are the per-vertex principal curvatures. |
| | 42 | S: Max | |
| | 43 | S: Avg | |
| | 44 | S: Skew | |
| | 45 | Curvedness (C): Min | Curvedness captures information on less sharp folding thus revealing smaller bumps and ridges. |
| | 46 | C: Max | |
| | 47 | C: Avg | |
| | 48 | C: Skew | $C = \sqrt{\left(\dfrac{k_1^2 + k_2^2}{2}\right)}$ |
| | 49 | Shape Index (SI): Min | |
| | 50 | SI: Max | $SI = \dfrac{2}{\pi}\tan^{-1}\left(\dfrac{k_1 + k_2}{k_2 - k_1}\right)$ |
| | 51 | SI: Avg | |
| | 52 | SI: Skew | |
| | 53 | Intrinsic Curvature Index (ICI) | ICI counts the number of regions with undulations or saliencies on the surface. $ICI = \dfrac{1}{4\pi} \int\int |k_{min} k_{max}|\, dA$ where $k_{min} = H - \sqrt{H^2 - G}$ $k_{max} = H + \sqrt{H^2 - G}$ |
| | 54 | Extrinsic Curvature Index (ECI) | ECI counts the number and length (with respect to the diameter) cracks and gaps on the surface. $ECI = \dfrac{1}{4\pi} \int\int |k_{mx}|(|k_{max}| - |k_{min}|)\, dA$ |
| Morpheme | 55 | Morpheme Distribution | The distribution of a plurality morphometric exemplars of the nodule surface. |
| | 56 | SILA Morpheme | Score Indicative of Lesion Abnormality based on the morpheme distribution. |
| | 57 | Morpheme Curvedness (MC): Avg | Morpheme-wise average curvedness of the surface. |

TABLE 1-continued

| Metric Category | # | Radiomic parameter | Non-Limiting Exemplary Description of radiomic parameter |
|---|---|---|---|
| | 58 | MC: Skew | Morpheme-wise skew of curvedness of the surface. |
| | 59 | Local SILA: Avg | Local morpheme SILA was computed by finding 2-ring neighbors around each vertex. The average and skew of the local SILA distribution may be computed. |
| | 60 | Local SILA: Skew | |
| | 61 | Local SILA: Histogram | Average cumulative distribution of the local morpheme SILA for the benign and malignant nodules |

Though not limiting, the list of parameters provided in Table 1 provides keys and criteria upon which the present disclosure can generate reports at process block 312 that communicate clinically-valuable information that is not otherwise available. That is, the report provided at process block 312 can tell a clinician if a mass is benign or malignant, even when the underlying images are inconclusive or, worse, by all prior studies applying known analysis, would provide a false indication of the mass being benign or malignant.

Nodule Surface Characteristic

In some aspects, the method 300 includes extracting 308 one or more surface characteristic parameter from the region of interest within the CT image. The one or more nodule surface characteristic parameter may be based on curvature shape descriptors of the surface of the indeterminate nodule. The curvature shape descriptors may be computed, for example, by meshing the CT imaging data to generate mesh vertices across the surface of the indeterminate nodule (e.g., reconstructing the CT imaging data to generate a mesh grid to characterize the surface of the indeterminate nodule). Optionally, the CT imaging data may be smoothed and cleaned (e.g., by applying a filter) before assigning CT imaging data points to mesh vertices. A parameter indicative of curvature, such as the mean or Gaussian curvature, is then computed using the mesh vertices and may be used to characterize the surface of the indeterminate nodule. Based on the vertex-wise signs of the curvatures, the mesh vertices may be classified into surface features, such as a peak, a ridge, a saddle ridge, a flat region, a minimal point or region, a pit, a valley, and/or a saddle valley.

Nodule Texture Via a Score Indicative of Lesion/Lung Aggression/Abnormality (SILA)

In accordance with some aspects of the present disclosure, a metric dubbed "Score Indicative of Lesion/Lung Aggression/Abnormality" (SILA) can be generated to assist in classifying indeterminate nodules as malignant or benign. In one aspect, SILA provides a metric indicative of radiomic distributions within the region of interest, for example image-based texture distributions (e.g., nominal texture exemplar distributions) and/or image-based surface distributions (surface exemplar distributions). In some aspects, the SILA metric may be computed by using spatial reasoning and multi-dimensional scaling. For example, the SILA metric may be computed by tagging at least a portion of the image segments 406. Image segments 406 may be tagged based on radiomic parameter values or qualitative features. Once an image segment 406 has been tagged the initial radiomic parameter value in the image segment 406 is compared to other candidate image segments based on a pair-wise similarity score between the initial value of the radiomic feature and the candidate image segment. To identify the similarity metric that best characterizes a match, a multi-dimensional scaling (MDS) may be used to project pairwise similarities between each of the voxels or image segments 406.

As described above, the multivariate similarity measure can be projected into three dimensions, to visualize trends and groupings. Using the pairwise similarity matrix, MDS positions the data such that the Euclidean distances (other distances are also possible) between all pairs of the points in this plot reflect the observed distances as faithfully as possible.

Studies:

The following examples of studies set forth, in detail, ways in which the above-described systems, methods, and techniques may be developed and performed in particular non-limiting applications. The following examples are presented by way of illustration and are not meant to be limiting in any way.

In the following example, the development of a radiomics-based approach for the classification of screen-detected indeterminate nodules using multivariate models is illustrated.

Subject Selection:

All participants for the present study were selected from the pool of eligible participants in the NLST, and all patient data were fully anonymized. The methods of the NLST have been published elsewhere. Briefly, the NLST was a randomized controlled trial conducted at 33 US centers, approved by the Institutional review boards at all centers. The study recruited asymptomatic high-risk individuals from August 2002 through April 2004, aged 55 to 74 years, with a smoking history of at least 30 pack-years, who quit 15 years or less prior to randomization. Individuals were screened with either annual low-dose CT or chest X-ray for three years and followed through Dec. 31, 2009. 26,722 individuals were randomized to the low-dose CT arm, and over 10,000 nodules (4-30 mm in longest diameter) were detected during the screening rounds.

Participants for the present study were selected from the pool of eligible participants in the NLST, who did not withdraw from follow-up, in the CT arm of the study (N=26,262) and included all screen-detected lung cancer cases: adenocarcinomas, squamous cell carcinomas, large cell carcinomas, small cell carcinomas and carcinoid tumors. Non-lung cancer controls were selected as a stratified random sample from all participants without a diagnosis of lung cancer during the screen or follow-up periods of the NLST.

Screening HRCT Data:

All NLST screening scans in this Example were low-dose scans with 2.5 mm collimation or less as pre-defined by strict NLST criteria. The CT datasets were obtained from the Lung Screening Study core laboratory and transferred to a hard drive that was shipped to the investigators. The datasets from the American College of Radiology Imaging Network core laboratory were transferred initially via hard drive, then electronically to the investigators. Information on nodule location was available to the investigators in the NLST database and confirmed by one radiologist and two pulmonologists using the CT obtained closest in time to the diagnosis of malignant or benign lung nodules. Nodules were electronically tagged for segmentation and analysis.

Multivariate Model:

Quantitative methods are developed herein to characterize independent radiological variables assessing various radiologic nodule features. Univariate analysis of the discriminatory power of each radiologic variable and receiver operative curve (ROC) analysis are performed for each variable and an area under the curve (AUC) is calculated. Statistical significance is calculated and adjusted for multiple comparisons using Bonferroni correction. Spearman rank correlations between all pairs of variables were calculated and displayed via a heat map. This data is shown in Table 2. Multivariate analysis was performed using least absolute shrinkage and selection operator (LASSO) method for both variable selection and regularization in order to enhance the prediction accuracy and interpretability of the multivariate statistical model. To increase the stability of the modeling, LASSO was run 1,000 times and the variables that were selected by at least 50% of the runs were included into the final multivariate model.

TABLE 2

| ID | Variables | Cancer mean (SD) n = 408 | Control mean (SD) n = 318 | AUC | P value |
|---|---|---|---|---|---|
| | 1. Location | | | | |
| 20 | Location | 6.37 (3.42) | 7.06 (3.16) | 0.56 | 0.00558 |
| 1 | Centroid_x | 154.78 (74.5) | 142.21 (78.73) | 0.56 | 0.02837 |
| 2 | Centroid_y | 143.95 (47.18) | 151.84 (55.47) | 0.47 | 0.03916 |
| 3 | Centroid_z | 203.38 (60.1) | 186.88 (65.91) | 0.57 | 0.00052 |
| | 2. Size | | | | |
| 4 | Volume* | 3305.34 (6361.01) | 345.45 (819.51) | 0.90 | 2.55e−20 |
| 5 | Surface Area* | 1673.08 (2150.55) | 345.04 (501.95) | 0.87 | 4.45e−23 |
| | 3. Shape | | | | |
| 6 | Sphericity | 0.51 (0.21) | 0.6 (0.29) | 0.58 | 1.24e−05 |
| 7 | Sphere Fit Factor | 6.82 (8.31) | 5.28 (5.82) | 0.58 | 0.00724 |
| 8 | Estimated Radius | 7.61 (3.99) | 3.59 (1.57) | 0.90 | 5.34e−37 |
| 9 | Minimum Enclosing Brick x | 19.82 (12.12) | 9.46 (5.51) | 0.84 | 6.21e−29 |
| 10 | Minimum Enclosing Brick y | 19.63 (12.13) | 10.11 (6.72) | 0.82 | 3.11e−26 |
| 11 | Brick | 16.49 (14.51) | 4.97 (2.65) | 0.92 | 1.24e−36 |
| 12 | Maximum Brick length | 24.08 (16.27) | 11.31(7.04) | 0.84 | 6.69e−29 |
| 13 | Elongation | −0.25 (0.4) | −0.31 (0.47) | 0.57 | 0.0737 |
| 14 | Flatness | −0.56 (0.99) | −1.01 (1.05) | 0.66 | 7.33e−09 |
| | 4. Radiodensity | | | | |
| 15 | HU_mean | −209.18 (163.55) | −465.23 (201.91) | 0.83 | 1.52e−40 |
| 16 | HU_variance | 614546.92 (3444392.14) | 295011.7 (609422.64) | 0.56 | 0.0969 |
| 17 | HU_skew | −2.64 (10.09) | −2.39 (1.2) | 0.56 | 0.665 |
| 18 | HU_kurtosis** | 31.36 (91.51) | 10.55 (10.05) | 0.74 | 7.19e−12 |
| 19 | HU_entropy | 7.89 (1.77) | 6.76 (1.76) | 0.82 | 1.20e−22 |
| | 5. Texture Nodule | | | | |
| 21 | SILA_Tex | 122.91 (34.32) | 58.62 (38.1) | 0.88 | 2.56e−47 |
| 22 | Texture_Risk | 2.17 (0.57) | 1.36 (0.54) | 0.82 | 7.47e−42 |
| | 6. Texture Nodule Surrounding Lung | | | | |
| 23 | Vessels | 1.88 (2.8) | 0.75 (1.29) | 0.74 | 2.42e−13 |
| 24 | Background | 9.49 (9.56) | 9.59 (11.25) | 0.52 | 0.886 |
| 25 | SILA_Fibrosis | 32.32 (17.84) | 27.42 (22.96) | 0.57 | 0.00141 |
| 26 | SILA_low attenuation | 35.54 (6.33) | 32.69 (19.86) | 0.55 | 0.0363 |
| | 7. Nodule Surface | | | | |
| 27 | Number of Vertices | 2711.4 (4745.67) | 515.25 (697.45) | 0.88 | 4.97e−24 |
| 28 | Number of Faces | 5419.18 (9488.83) | 1026.56 (1395.09) | 0.88 | 5.05e−24 |
| 29 | Willmore Bending Energy_2 | 1574.75 (3792.16) | 480.61 (721.39) | 0.75 | 1.27e−12 |
| 30 | Willmore Bending Energy | 2269.82 (6283.03) | 802.67 (1116.04) | 0.70 | 1.01e−09 |
| 31 | Minimum Mean Curvature | −0.92 (0.65) | −0.28 (0.46) | 0.82 | 4.37e−31 |
| 32 | Maximum Mean Curvature | 3.57 (2.44) | 3.27 (1.82) | 0.51 | 0.0731 |
| 33 | Average Positive Mean Curvature | 0.34 (0.11) | 0.58 (0.2) | 0.87 | 3.73e−39 |
| 34 | Skew Positive Mean Curvature | 2.89 (2.04) | 2.01 (1.2) | 0.66 | 2.15e−10 |
| 35 | Minimum Gaussian Curvature | −1.01 (0.87) | −0.87 (0.84) | 0.58 | 0.0381 |
| | Maximum Gaussian | | | | |

TABLE 2-continued

| ID | Variables | Cancer mean (SD) n = 408 | Control mean (SD) n = 318 | AUC | P value |
|---|---|---|---|---|---|
| 36 | Curvature Average positive | 15.43 (30.41) | 12.6 (21.14) | 0.52 | 0.172 |
| 37 | Gaussian Curvature Skew Positive | 0.29 (0.29) | 0.61 (0.52) | 0.79 | 7.37e−21 |
| 38 | Gaussian Curvature | 7.57 (3.82) | 4.66 (2.09) | 0.78 | 1.46e−24 |
| 39 | Minimum Sharp | 8.82e−05 (9.35e−04) | 8.86e−04 (2.41e−03) | 0.79 | 6.01e−07 |
| 40 | Maximum Sharp | 38.99 (62.98) | 22.44 (52.57) | 0.59 | 0.00028 |
| 41 | Average Sharp | 0.59 (0.43) | 1.01 (0.78) | 0.71 | 1.89e−15 |
| 42 | Skew Sharp | 7.95 (7.45) | 4.25 (3.53) | 0.72 | 3.16e−12 |
| 43 | Minimum Curved | 0.01 (0.03) | 0.07 (0.1) | 0.82 | 6.44e−18 |
| 44 | Maximum Curved | 5.72 (4.21) | 4.8 (3.05) | 0.53 | 0.00143 |
| 45 | Average Curved | 0.58 (0.19) | 0.96 (0.32) | 0.86 | 1.89e−38 |
| 46 | Skew Curved | 2.87 (2.26) | 1.79 (1.25) | 0.69 | 5.44e−12 |
| 47 | Minimum Shape Index | −0.98 (0.01) | −0.98 (0.02) | 0.63 | 9.85e−07 |
| 48 | Maximum Shape Index | 0.98 (0.16) | 0.55 (0.61) | 0.82 | 1.46e−17 |
| 49 | Average Shape Index | −0.29 (0.18) | −0.55 (0.13) | 0.88 | 5.51e−43 |
| 50 | Skew Shape Index | 1.63 (0.91) | 1.72 (1.42) | 0.54 | 0.306 |
| | Intrinsic Curvature | | | | |
| 51 | Index | 37.78 (118.81) | 15.7 (21.56) | 0.64 | 1.49e−06 |
| | Extrinsic Curvature | | | | |
| 52 | Index | 113.69 (284.16) | 39.41 (57.05) | 0.73 | 5.04e−11 |
| | 8. Distribution of the nodule surface exemplars | | | | |
| 53 | SILA morpheme | 36.02 (11.24) | 19.71 (12.61) | 0.84 | 5.21e−40 |
| | Morpheme Average | | | | |
| 54 | Curvature Morpheme Skew | 0.74 (0.23) | 1.05 (0.32) | 0.81 | 1.10e−29 |
| 55 | Curvature | 2.33 (1.73) | 1.57 (1.04) | 0.66 | 4.20e−10 |
| 56 | Local SILA Average | 27.65 (8.71) | 15.3 (9.26) | 0.84 | 5.08e−40 |
| 57 | Local SILA Skew | 0.71 (0.42) | 0.49 (0.68) | 0.60 | 1.46e−07 |

\*: One case (ID 516) is the outlier and was removed from the calculations.
\*\*: One case (ID 534) is the outlier and was removed from the calculations.

Study Participants:

649 LDCT were reviewed of cancers diagnosed in the screening arm of the NLST that included 353 adenocarcinomas, 136 squamous cell carcinomas, 28 large cell carcinomas, 75 non-small cell carcinomas, 49 small cell carcinomas and 5 carcinoid tumors. 408 LDCT scans with malignant nodules were selected and analyzed that included 290 adenocarcinomas, 81 squamous cell carcinomas, 19 large cell carcinomas, 14 small cell lung cancers, and 4 carcinoid tumors. A stratified random sample of non-lung cancer control nodules (size between 7 and 30 mm) was selected on a 1:1 basis, and 318 benign nodules were selected and included in the analysis. The demographic and clinical characteristics of individuals included in the study are summarized in Table 3. Quantitative methods were developed to characterize independent radiological variables assessing various radiologic nodule features including 1. Nodule location, 2. Nodule size, 3. Nodule shape, 4. Nodule radiodensity 5. Nodule texture, 6. Texture/radiodensity of the nodule-free surrounding lung, 7. Nodule surface characteristics and 8. Distribution of the nodule surface characteristics exemplars using 726 nodules identified from the NLST dataset (benign, n=318 and malignant, n=408).

TABLE 3

| | Lung Cancer Cases (n = 408) | Nodule-Positive Controls (n = 318) | P Value |
|---|---|---|---|
| Age, mean ± SD, y | 63.7 ± 5.3 | 61.2 ± 5.0 | <0.001 |
| Sex, n (%) | | | 0.45 |
| Male | 230 (56.4) | 189 (59.4) | |
| Female | 178 (43.6) | 129 (40.6) | |
| Race, n (%) | | | 0.03 |
| White | 385 (94.4) | 286 (89.9) | |
| Black, Asian, other | 23 (5.6) | 32 (10.1) | |
| Ethnicity, n (%) | | | 0.31 |
| Hispanic or Latino | 405 (98.4) | 313 (99.3) | |
| Neither Hispanic nor Latino | 3 (1.6) | 5 (0.7) | |
| Smoking, n (%) | | | 0.37 |
| Current | 221 (54.2) | 161 (50.6) | |
| Former | 187 (45.8) | 157 (49.4) | |
| Pack-years smoked, mean ± SD | | | |
| Current smokers | 64.8 ± 25.8 | 55.5 ± 20.9 | <0.001 |
| Former smokers | 66.7 ± 30.6 | 55.2 ± 26.9 | <0.001 |
| Self-reported history of COPD, n (%) | | | |
| Yes | 43 (10.5) | 18 (5.7) | 0.02 |
| No | 365 (89.5) | 300 (94.3) | |
| FH of lung cancer, n (%) | | | 0.08* |
| Yes | 113 (28.9) | 69 (22.8) | |
| No | 278 (71.1) | 233 (77.2) | |
| Missing | n = 17 | n = 16 | |
| Stage, n (%) | | | |
| I | 298 (73.0) | — | |
| II | 29 (7.1) | — | |
| III | 55 (13.5) | — | |
| IV | 20 (5.0) | — | |
| Carcinoid, unknown | 6 (1.5) | — | |

TABLE 3-continued

|  | Lung Cancer Cases (n = 408) | Nodule-Positive Controls (n = 318) | P Value |
|---|---|---|---|
| Histologic subtype, n (%) |  |  | — |
| Adenocarcinoma | 290 (71.1) | — |  |
| Squamous cell carcinoma | 81 (19.9) | — |  |
| Other, NOS, unknown | 37 (9.1) | — |  |

P Values calculated using Fisher's exact test for categorical variables, Student's t test for continuous variables.
*P value for family history of lung cancer was calculated without missing data.

Figure 5:
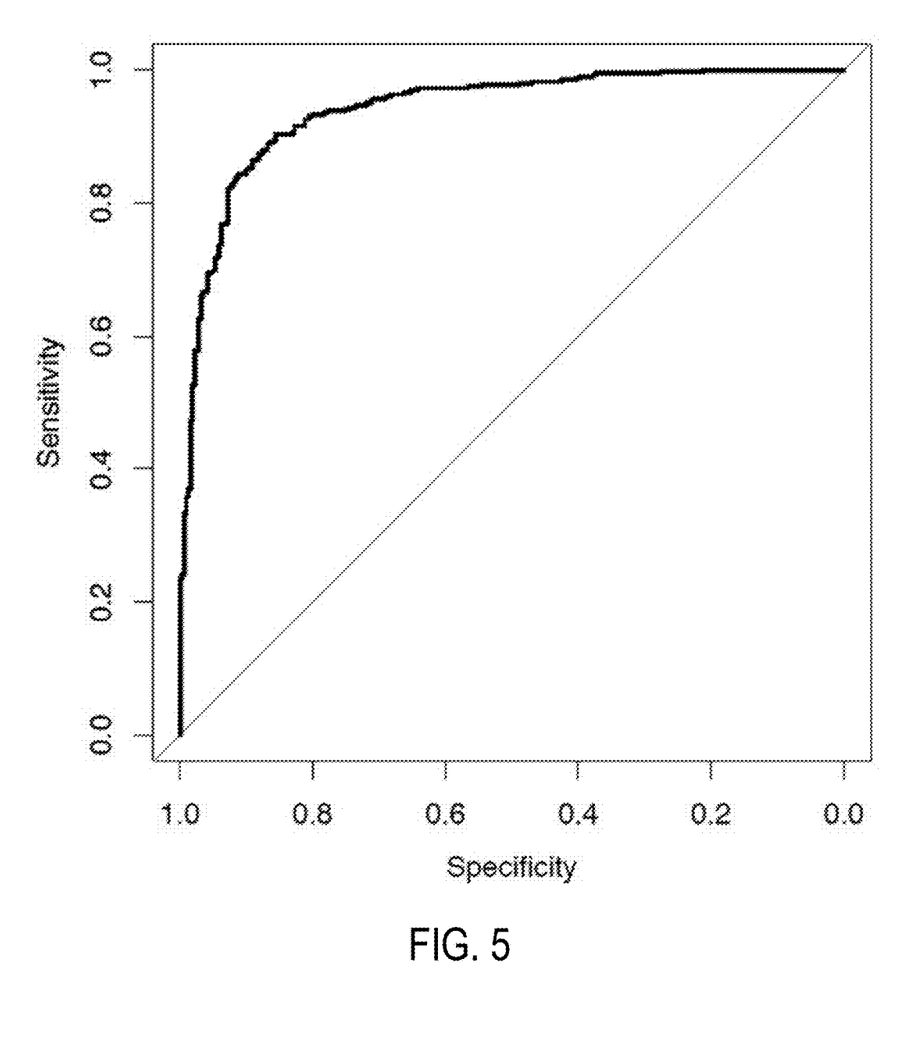
FIG. 5 is a receiver operating curve analysis in accordance with the present disclosure.

Multivariate Analysis:

In order to select the optimal variables, adjust the regression coefficients to optimize the transportability (external validity) of the model and determine the degree of optimism of the model and perform optimism-corrected analysis of the performance of the model by ROC analysis, all 57 quantitative imaging variables were included in the LASSO regression model. Multivariate analysis using LASSO on all features yielded a multivariate model with 8 selected features (selected with frequency>50% after introducing bootstrap to reduce variability after 1000 runs) with an AUC estimate of 0.941. (FIG. 5) These 8 features include: 1. Offset carina centroid_z (Nodule location), 2. Minimum enclosing brick (Nodule shape), 3. Nodule flatness (Nodule shape), 4. SILA nodule texture (Nodule texture), 5. Maximum shape index (Nodule surface Characteristics), 6. Average shape index (Nodule surface Characteristics), 7. Average positive mean curvature (Nodule surface Characteristics) and 8. Minimum mean curvature (Nodule surface Characteristics), all with P<0.01. To correct overfitting (internal validation) we used the bootstrapping technique to estimate the optimism of the AUC. The optimism-corrected AUC is 0.939 (FIG. 5). Using Youdan's index, we obtained the optimal cutoff at 0.478 with sensitivity 0.904 and specificity 0.855. A subset analysis of nodules with size between 7 mm and 15 mm yielded an AUC of 0.9477 with an optimism-corrected AUC of 0.9409 (n=169 nodules).

Offset carina centroid_z captures the location of the nodule in the vertical axis in relationship to the carina, the minimal enclosing brick and flatness capture shape and volume, SILA texture is a summary variable capturing the nodule texture, maximum and average shape index capturing the complexity of the nodule surface and average positive mean curvature and minimum mean curvature representing the degree of curvature of the outer surface of the nodule account for the surface characteristics of the nodule.

In conclusion, a radiomics CT-based approach is provided that can perform classification and reporting as malignant or benign, even when other systems and methods fail, and, thereby, can mitigate the risks inherent in cancer screening by minimizing unnecessary mortality, morbidity, radiation exposure, patient anxiety, and healthcare costs. This was further validated in additional studies.

Figure 6:
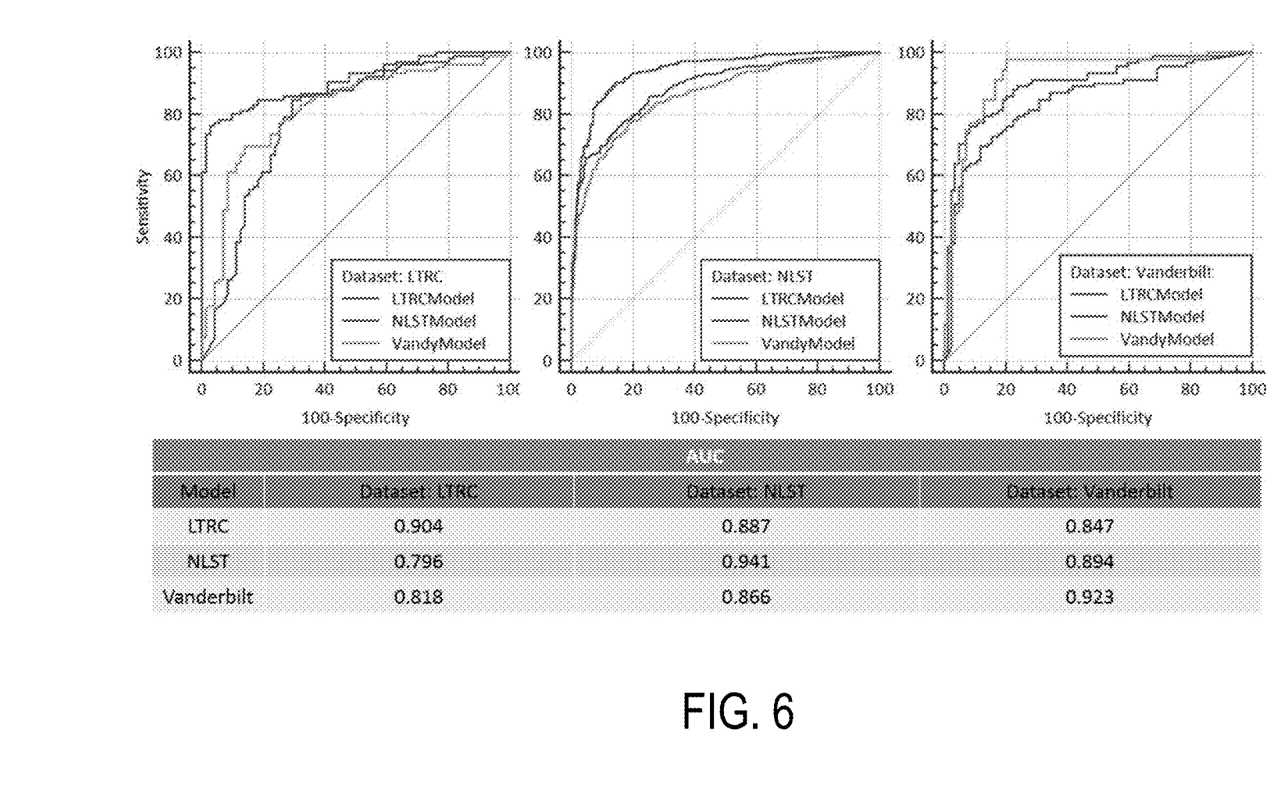
FIG. 6 is a set of correlated graphs showing performance of a cross-validation of systems and methods described herein in the NLST, LTRC and Vanderbilt University datasets.

In particular, referring to FIG. 6, the systems and methods described herein were cross-validated in a blinded fashion using two independent datasets of incidentally discovered pulmonary nodules. As illustrated, the systems and methods of the present disclosure identified and created a framework to utilize in an automated fashion, a multi-variant model of radiomics features to determine or predict the risk of malignancy among screen-detected masses, including indeterminate pulmonary nodules (≥7 mm in size). The systems and methods provided herein outperforms all assessed published and reported commercial and academic risk prediction models and is independent of mass or nodule size. The systems and methods provided herein has been validated in two independent datasets of incidentally discovered pulmonary nodules (high-risk LTRC and Vanderbilt datasets), as illustrated in FIG. 6.

The systems and methods provided herein provide the basis for significant changes in management of screening- and incidentally-identified masses, including lung nodules. The ability to identify non-invasively benign and malignant lesions, as provided herein, avoids unnecessary delays in aggressive management and results in improved outcomes. Based on the screening criteria proposed by the US Preventative Service Task Force, 10 million individuals are eligible for lung cancer screening in the US alone, an estimated 40% of these individuals will have suspicious findings on screening CT. The ability to distinguish benign from malignant nodules as provided herein would avoid unnecessarily aggressive treatments such as lobectomy associated with significant morbidity (increased dyspnea on exertion, 63%; dyspnea with minimal activity, 32%; and inability to leave the home, 11%), mortality (1%-4% operative mortality for lobectomy), and health care costs.

The present invention has been described in terms of one or more preferred embodiments, and it should be appreciated that many equivalents, alternatives, variations, and modifications, aside from those expressly stated, are possible and within the scope of the invention.

We claim:

1. A method for generating an imaging report indicating an indeterminate nodule in a subject's lung as malignant or benign by performing a quantitative analysis on a computed tomography (CT) image of the subject, the method comprising:
    (a) identifying, using a computer system, a region of interest in the CT image that includes the indeterminate lung nodule;
    (b) segmenting, using the computer system, the image to delimit at least a portion of the region of interest into segments;
    (c) tagging, using the computer system, at least a portion of the image segments based on at least one initial radiomic parameter value;
    (d) determining, using the computer system, a metric indicative of a nodule texture distribution or nodule surface distribution in the region of interest by comparing the tagged image segments having the at least one initial radiomic parameter value to a candidate image segment using a similarity metric, and performing multi-dimensional scaling (MDS) to project pairwise similarities between the tagged image segments and the candidate image segment to generate the metric indicative of the nodule texture distribution or the nodule surface distribution in the region of interest;
    (e) extracting, using the computer system, a set of radiomic parameters indicative of the indeterminate lung nodule, wherein the set of radiomic parameters include one or more nodule location parameter, one or more nodule shape parameter, one or more nodule surface characteristic parameter, and the metric indicative of the nodule texture distribution or nodule surface distribution; and
    (f) generating, using the computer system, a report classifying the indeterminate lung nodule as being malignant or benign based on the set of radiomic parameters.

2. The method of claim 1, wherein classifying the indeterminate nodule further includes applying the set of radiomic parameters to a multivariate predictive model, and discerning if the indeterminate lung nodule is malignant or benign based on an output of the multivariate predictive module.

3. The method of claim 1, wherein the one or more nodule location parameter includes a coordinate offset location associated with a centroid of the indeterminate nodule within the CT image, wherein the coordinate offset location is identified relative to an origin in the CT image.

4. The method of claim 3, wherein the origin is taken as the Carina, Hila, or Pleura in the subject's lung.

5. The method of claim 3, wherein the one or more nodule location parameter includes a z coordinate associated with the centroid of the indeterminate nodule, and wherein the origin is taken as the Carina in the subject's lung.

6. The method of claim 1, wherein the one or more nodule shape parameter is selected from the group consisting of a minimum enclosing brick and flatness.

7. The method of claim 1, wherein the one or more nodule surface characteristic parameter is selected from a shape index and a curvature from within the region of interest.

8. The method of claim 7, wherein the shape index is selected from a maximum shape index and an average shape index from within the region of interest.

9. The method of claim 7, wherein the mean curvature is selected from an average positive mean curvature and a minimum mean curvature from within the region of interest.

10. The method of claim 1, wherein the similarity metric is a Cramer Von Mises distance.

11. The method of claim 1, wherein the set of radiomic parameters includes a plurality of nodule shape parameters, a plurality of nodule surface characteristic parameters, the one or more nodule texture distribution parameter, and the one or more location parameter.

12. The method of claim 9, wherein the set of radiomic parameters includes two nodule shape parameters, and four nodule surface characteristic parameters.

13. The method of claim 1, wherein the set of radiomic parameters further includes one or more parameter associated with the surrounding tissue of the indeterminate lung nodule.

14. The method of claim 1, wherein the set of radiomic parameters further includes a nodule radiodensity parameter.

15. The method of claim 1, wherein the set of radiomic parameters further includes one or more nodule surface characteristic distribution parameter.

16. The method of claim 2, wherein classifying the indeterminate lung nodule as being malignant or benign further includes applying clinical characteristics associated with the subject's medical history to the multivariate predictive model.

17. The method of claim 1, wherein conducting segmentation to delimit at least a portion of the indeterminate lung nodule further includes a region growing technique based on one or more nodule texture parameter of the image segments within a operator specified bounding cube.

18. A method for classifying an indeterminate lung nodule in a subject as malignant or benign by performing a quantitative analysis on computed tomography (CT) imaging data of the subject's lung, the method including using a processor to perform steps comprising:
identifying a region of interest in the indeterminate lung nodule in the CT imaging data;
segmenting the CT imaging data to delimit at least a portion of the indeterminate lung nodule into image segments;
extracting a set of radiomic parameters indicative of the indeterminate lung nodule, wherein the set of radiomic parameters include:
one or more nodule location parameter that includes an offset coordinate location associated with a centroid of the indeterminate lung nodule within the CT imaging data, wherein the offset coordinate location is identified relative to an origin in the CT imaging data;
one or more nodule texture parameter,
two nodule shape parameters, and
four nodule surface characteristic parameters;
generating a report classifying the indeterminate lung nodule as being malignant or benign based on the set of radiomic parameters of the indeterminate lung nodule.

19. A system comprising:
a memory having stored therein computed tomography images of a subject;
a processor configured to access the memory and carry out steps comprising:
(a) identify a region of interest in the CT images that includes a tissue mass;
(b) segment the images to delimit at least a portion of the region of interest into segments;
(c) tag at least a portion of the image segments based on at least one initial radiomic parameter value;
(d) determine a metric indicative of a nodule texture distribution or nodule surface distribution in the region of interest by comparing the tagged image segments having the at least one initial radiomic parameter value to a candidate image segment using a similarity metric, and perform multi-dimensional scaling (MDS) to project pairwise similarities between the tagged image segments and the candidate image segment to generate the metric indicative of the nodule texture distribution or the nodule surface distribution in the region of interest;
(e) extract a set of radiomic parameters indicative of the tissue mass, wherein the set of radiomic parameters include one or more of tissue mass location, tissue mass shape, tissue mass surface characteristic, or the metric indicative of the nodule texture distribution or nodule surface distribution; and
(f) generate a report classifying the indeterminate lung nodule as being malignant or benign based on the set of radiomic parameters.

20. The system of claim 19 wherein the system forms a computed tomography system.

* * * * *